United States Patent [19]

Abdulla et al.

[11] Patent Number: 4,619,686
[45] Date of Patent: Oct. 28, 1986

[54] PYRIDAZINYLUREA COMPOUNDS AND METHODS OF USE AS HERBICIDES

[75] Inventors: Riaz F. Abdulla, Greenfield; Jack G. Samaritoni, Knightstown, both of Ind.

[73] Assignee: Eli Lilly and Company, Indianapolis, Ind.

[21] Appl. No.: 631,651

[22] Filed: Jul. 17, 1984

[51] Int. Cl.$^4$ .................. A01N 43/58; G07D 237/20; G07D 237/22
[52] U.S. Cl. ...................... 71/92; 544/224; 544/238; 544/239; 544/240; 544/241
[58] Field of Search ...................... 544/224, 238; 71/92

[56] References Cited
U.S. PATENT DOCUMENTS

| | | | |
|---|---|---|---|
| 3,469,965 | 9/1969 | Bruce | 71/68 |
| 3,947,437 | 3/1976 | Johnston | 71/92 |
| 4,093,444 | 6/1978 | Clapot et al. | 71/92 |
| 4,144,338 | 3/1979 | Bolhofer | 424/251 |
| 4,331,807 | 5/1982 | Okamoto | 544/224 |

FOREIGN PATENT DOCUMENTS 52668 6/1982 European Pat. Off. .
58-077866 4/1981 Japan .

OTHER PUBLICATIONS

Ohsawa, A., et al., "Thermal Decomposition of 2H-[1,2,4]Oxadiazolo[2,3-a]pyridine-2-thione and 2H-[1,2,4]-Oxadiazolo[2,3-b]-pyrdiazine-2-thione", *Heterocycles*, 12(7), 917-920 (1979) See p. 919, when $X=N$.

Ohsawa, A., et al., in "Thermal Decomposition of 2H-[1,2,4]Oxadiazolo[2,3-α]pyridine-2-thione and 2H-[1,2,4]-Oxadiazolo[2,3-b]-pyridazine-2-thiones: Generation of Aza-heteroaromatic α-Isocyanates and Their Utilization for the Synthesis of Unsymmetrical Disubstituted Ureas", *Chem. Pharm. Bull.*, 28(12), 3570-3575 (1980) p. 3572, Table II, 18-25; pp. 3574-3575.

Stanovnik, B., et al., in "Heteroacyl Azides as Acylating Agents for Aromatic or Heteroaromatic Amines (1)", *J. Heterocyclic Chem.* 17(4), 733-736 (1980) p. 735, Example 15-16.

Stanovnik, B., et al., in "Reactions of N-Heteroaryl--formamide Oximes and N-Heteroacylacetamide Oximes with N,N-Dimethylformamide Dimethyl Acetal, Synthesis of 2-Methyl-s-triazolo[1,5-x]azines and N-Methylcyanoaminoazines", *J. Heterocyclic Chem.* 19(3), 577-583 (1982) See No. 13 on pp. 579 and 582.

Zupan, M., et al., in "Pyridazines. LI. Synthetic Approaches to Pyridazino[2,3,-a]-1,3,5-Triazines, A Novel Heterocyclic System", *J. Org. Chem.*, 37(19), 2960-2963 (1972).

*Primary Examiner*—Donald G. Daus
*Assistant Examiner*—Stephen M. Kapner
*Attorney, Agent, or Firm*—Kathleen R. S. Page

[57] ABSTRACT

This invention describes noval pyridazinylurea compounds, which are useful as herbicides.

16 Claims, No Drawings

PYRIDAZINYLUREA COMPOUNDS AND METHODS OF USE AS HERBICIDES

BACKGROUND OF THE INVENTION

This invention belongs to the field of agricultural chemistry and provides a class of new herbicidal compounds, herbicidal methods, and formulations making use of the compounds.

SUMMARY OF THE INVENTION

This invention provides pyridazinylurea compounds of the formula (I):

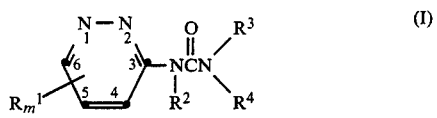

wherein $R^1$ is halo, trifluoromethyl, $C_1$–$C_8$ alkyl, $C_3$–$C_6$ cycloalkyl, ($C_1$–$C_3$ alkyl)$C_3$–$C_6$ cycloalkyl, ($C_1$–$C_3$ alkoxy)$C_1$–$C_8$ alkyl, adamantyl, phenoxy, phenyl, or halo-substituted phenyl;

$R^2$ is hydrogen, $C_1$–$C_6$ alkyl or $C_2$–$C_6$ alkenyl;

$R^3$ and $R^4$ are independently $C_1$–$C_6$ alkyl, $C_1$–$C_6$ alkoxy, $C_2$–$C_6$ alkenyl, ($C_1$–$C_6$ alkoxy)$C_1$–$C_6$ alkyl, di($C_1$–$C_4$ alkoxy)$C_1$–$C_6$ alkyl, (hydroxy)$C_1$–$C_6$ alkyl, phenyl, benzyl, (carboxy)$C_1$–$C_6$ alkyl, or ($C_1$–$C_6$ acyloxy)$C_1$–$C_6$ alkyl; or together with the nitrogen form a ring such as piperidine, morpholine, or pyrrolidine, and m is an integer from 1 to 3; provided that not more than one of $R^3$ and $R^4$ is $C_1$–$C_6$ alkyl.

Also provided by this invention is a method of inhibiting the growth of unwanted vegetation which comprises contacting the vegetation or the soil in which the vegetation is growing with a herbicidally-effective amount of a pyridazinylurea compound of the formula (II):

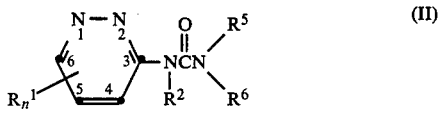

wherein $R^1$ and $R^2$ are defined as above; and $R^5$ and $R^6$ are independently hydrogen, $C_1$–$C_6$ alkyl, $C_1$–$C_6$ alkoxy, $C_2$–$C_6$ alkenyl, ($C_1$–$C_6$ alkoxy)$C_1$–$C_6$ alkyl, di($C_1$–$C_4$ alkoxy)$C_1$–$C_6$ alkyl, (hydroxy)$C_1$–$C_6$ alkyl, phenyl, benzyl, (carboxy)$C_1$–$C_6$ alkyl, or ($C_1$–$C_6$ acyloxy)$C_1$–$C_6$ alkyl; or together with the nitrogen form a ring such as piperidine, morpholine, or pyrrolidine; and n is an integer from 0 to 3.

Further provided are formulations comprising the pyridazinylurea compounds of the formula (I) and agriculturally-acceptable carriers therefor.

DESCRIPTION OF THE INVENTION

In addition to the compounds of formula (I), there is also provided a preferred group of compounds wherein:

$R^1$ is halo or $C_1$–$C_4$ alkyl;

$R^2$ is hydrogen;

$R^3$ and $R^4$ are independently $C_1$–$C_3$ alkyl, $C_1$–$C_3$ alkoxy, $C_2$–$C_4$ alkenyl, hydroxy($C_1$–$C_4$ alkyl) or ($C_1$–$C_6$ acyloxy)$C_1$–$C_6$ alkyl; and m is 1 or 2; provided that not more than one of $R^3$ and $R^4$ is $C_1$–$C_3$ alkyl. There is a preferred group of compounds of the formula (II) for use in the herbicidal method wherein:

$R^1$ is halo or $C_1$–$C_4$ alkyl;

$R^2$ is hydrogen;

$R^5$ and $R^6$ are independently hydrogen, $C_1$–$C_3$ alkyl, $C_1$–$C_3$ alkoxy, $C_2$–$C_4$ alkenyl, hydroxy($C_1$–$C_4$ alkyl), or ($C_1$–$C_6$ acyloxy)$C_1$–$C_6$ alkyl; and n is 1 or 2.

Some of the preferred compounds of the formula (I) or (II) include:

N'-[6-chloro-5-(1,1-dimethylethyl)-3-pyridazinyl]-N,N-dimethylurea;

N'-[6-chloro-5-(1,1-dimethylethyl)-3-pyridazinyl]-N-methoxy-N-methylurea;

N-[2-(acetyloxy)ethyl]-N'-[6-chloro-5-(1,1-dimethylethyl)-3-pyridazinyl]-N-methylurea; and N'-[6-chloro-5-(1,1-dimethylethyl)-3-pyridazinyl]-N-(2-hydroxyethyl)-N-methylurea.

The following defines the various terms used in this application.

The term "$C_1$–$C_8$ alkyl" refers to the straight and branched aliphatic groups of one to eight carbon atoms including ethyl, propyl, isopropyl (1-methylethyl), butyl, methyl, isobutyl (2-methylpropyl), sec-butyl (1-methylpropyl), tert-butyl (1,1-dimethylethyl), pentyl, isopentyl (3-methylbutyl), sec-pentyl (1-methylbutyl), 1,1-dimethylpropyl, 1,2-dimethylpropyl, neopentyl (2,2-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like. The terms "$C_1$–$C_6$ alkyl","$C_1$–$C_4$ alkyl","$C_1$–$C_3$ alkyl" are also included in this definition.

The term "$C_1$–$C_6$ alkoxy" refers to the aliphatic groups of one to six carbon atoms attached to the remainder of the molecule by an oxygen atom, such as methoxy, ethoxy, propoxy, butoxy, and the like. The terms "$C_1$–$C_4$ alkoxy" and "$C_1$–$C_3$ alkoxy" are also included in this definition.

The halogens include bromine, chlorine, fluorine, and iodine.

The term "$C_3$–$C_6$ cycloalkyl" refers to saturated aliphatic rings of three to six carbon atoms, such as cyclopropyl, cyclobutyl, cyclopentyl, and cyclohexyl.

The term "$C_2$–$C_6$ alkenyl" refers to the straight and branched aliphatic group of two to six carbon atoms, which has one carbon to carbon double bond, and includes ethenyl, propenyl, butenyl, pentenyl, hexenyl, and the like.

The term "$C_1$–$C_6$ acyloxy" refers to acyl groups of one to six carbon atoms, which are attached to the remainder of the molecule by an oxygen atom, such groups include acetyloxy, and the like.

The term "halo-substituted phenyl" refers to a phenyl group, which is substituted by one to three halogen atoms, such as chlorophenyl, dichlorophenyl, trichlorophenyl, bromochlorophenyl, and the like.

Preparation of the Pyridazinylureas

The processes for making the pyridazinylurea compounds of formulae (I) and (II) are outlined below.

Preparation 1:

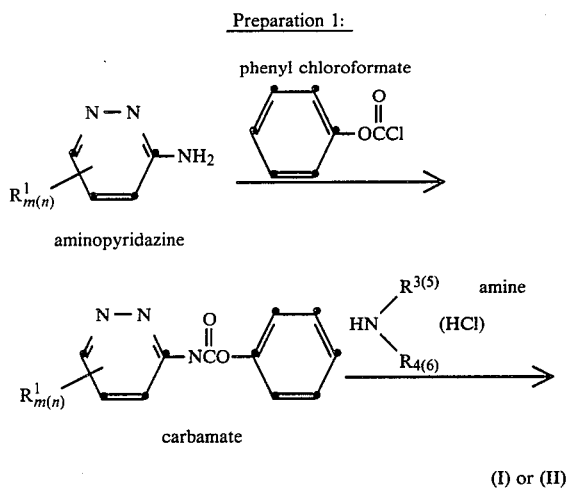

carbamate (I) or (II)

An aminopyridazine is reacted with phenyl chloroformate in the presence of an acid acceptor. Typically used as the acceptor is an inorganic or organic base, such as pyridine, which is preferred. This reaction forms the carbamate and may be optionally run in an inert organic solvent, such as toluene.

The resulting carbamate is dissolved in an inert organic solvent, such as DMF, THF, benzene, toluene, pyridine, methylene chloride, and the like, with benzene being the preferred solvent. Then the substituted amine of the formula $HNR^{3(5)} R^{4(6)}$ or $HNR^{3(5)} R^{4(6)} \cdot HCl$ is placed in an inert organic solvent, such as DMF, THF, benzene, toluene, pyridine, methylene chloride, and the like, with benzene or toluene being preferred. A strong organic base, such as 1,5-diazabicyclo[4.3.0]non-5-ene (DBN) and 1,5-diazabicyclo[4.3.0]undecene (DBU), is added to free the amine when using the salt. The carbamate is added and the contents are stirred for about 5 minutes to about 24 hours at a temperature of from about 20° to about 50° C. The preferred reaction conditions are about 25° C. for about 1 hour.

When an amino acid or amino ester salt is used as a starting material, the initially-formed urea of the formula (I) undergoes cyclization to a hydantoin. Treatment of the hydantoin with a base, such as aqueous sodium hydroxide, reopens the ring to give the desired urea.

After the reaction is complete, the solvent is removed under vacuum. The resulting compound is then isolated and purified, preferrably by silica gel chromatography.

Preparation 2:

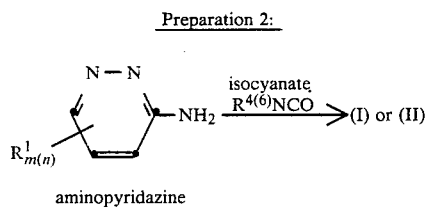

aminopyridazine

A compound of this invention can also be prepared by reaction of an aminopyridazine and an isocyanate in an inert organic solvent, such as THF, benzene, ethyl acetate, methylene chloride, and the like. The reaction is run at a temperature of from about 25° to about 100° C. for about ½ to about 24 hours.

Preparation 3:

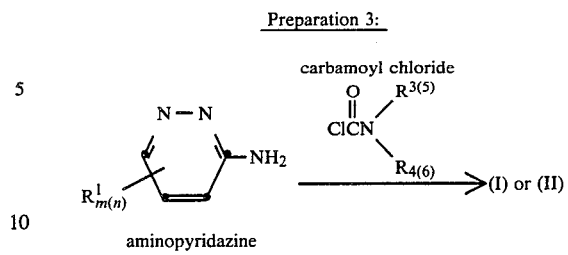

aminopyridazine

A carbamoyl chloride is dissolved in an inert organic solvent, such as dimethylsulfoxide (DMSO), dimethylformamide (DMF), and the like, and added to an aminopyridazine in an inert organic solvent such as DMSO, DMF, and the like.

The reaction mixture is maintained at a temperature from about 20° to about 100° C., preferably between 25° and 35° C. when using the sodium salt of the amine, for a period of from about 1 to about 24 hours. Following completion of the reaction, the reaction mixture is cooled and mixed with water or extracted with ether. Any resulting precipitate is recovered by filtration and dried. The precipitate can be further purified by recrystallization from typical solvents or solvent mixtures, such as benzene, hexane, chloroform, ether, and the like.

Preparation 4:

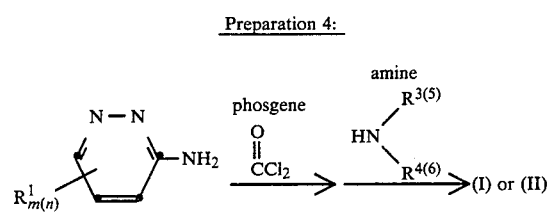

An aminopyridazine compound can also be reacted with phosgene followed by an amine. The pyridazine-phosgene reaction is run in the presence of hydrochloric acid. The reaction is carried out in an inert organic solvent, such as toluene, and the like, at elevated temperatures of about 60° to 110° C. The amine is then added (optionally in an inert organic solvent, such as toluene, chloroform, and the like) and the reaction run at a temperature from about 50° to about 100° C.

An excess of phosgene, in a ratio of from 3 to about 4 moles thereof to 1 mole of pyridazine, is preferably employed. During the reaction, excess phosgene can be removed by purging the reaction mixture with an inert gas, such as nitrogen.

The compounds of the formula (I) or (II) can also be prepared from other compounds of the formula (I) or (II). For example, compounds of the formula (I) or (II), which are hydroxyureas can be acylated. In addition, other substitutions can be made by those skilled in the art.

Preparation of Intermediates

The halopyridazine intermediate can be prepared by the reaction of a less substituted pyridazine with a carboxylic acid in the presence of peroxydisulfate ion, a catalytic amount of silver ion, and mineral acid, whose anion will not cause precipitation of the corresponding silver salt, all in an aqueous solvent system at a temperature from about 40° to about 80° C.

A pyridazine is reacted with a carboxylic acid. Silver (II) ion, generated from silver (I) ion and peroxydisulfate, is used in the oxidative decarboxylation of the carboxylic acid. The reaction is carried out in an aqueous solvent system with a mineral acid at a temperature from about 40° to about 80° C.

The silver ion is obtained from a water-soluble silver (I) salt, such as silver nitrate, silver fluoride, silver trifluoroacetate, silver perchlorate, and the like, with silver nitrate being preferred. The silver (I) salt is used in catalytic amounts in the reaction, but the actual catalyst generated is silver (II) ion.

Typical of the carboxylic acids are pivalic acid (trimethylacetic acid), n-butyric acid, isobutyric acid, propanoic acid, acetic acid, cyclobutanecarboxylic acid, cyclopropanecarboxylic acid, cyclopentanecarboxylic acid, 1-adamantanecarboxylic acid, phenoxyacetic acid, glycolic acid, and the like, with pivalic acid being preferred. The source of peroxydisulfate (persulfate) ion is from an ammonium peroxydisulfate or an alkali peroxydisulfate. Ammonium peroxydisulfate is preferred.

Typical of the aqueous solvent systems that can be used are water, water-acetonitrile, and the like with water being preferred. The mineral acids that can be used must be those whose anion will not cause precipitation of the corresponding silver salt. Such mineral acids include perchloric, trifluoroacetic, sulfuric, and the like, with sulfuric being preferred.

The reaction goes rapidly and no unusual excess of reagents is necessary. In general, stoichiometric amounts of the reagents are adequate. As is usual in organic chemistry, it may be economical to use an excess of less expensive reagents to assure that more expensive reagents are fully consumed.

The amount of reactants used varies with the particular reactants, but typically 0.05 to 1.0 equivalent of silver ion; 1.0 to 5.0 equivalents of carboxylic acid; 1.0 to 3.0 equivalents of mineral acid; and 1.0 to 2.0 equivalents of peroxydisulfate ion are used with respect to the pyridazine. The preferred amounts used are 0.1 equivalent of silver and 1.0–1.75 equivalents of peroxydisulfate. The amounts of reactants used also vary with the desired amount of alkylation. In the case of dialkylation, the amount of peroxydisulfate, silver, and carboxylic acid used can be increased.

Usually the pyridazine starting material, silver salt, carboxylic acid, and mineral acid are all in an aqueous solvent system and heated to about 40° to 80° C. Maintaining the temperature, a solution of peroxydisulfate in water is added dropwise. The reaction is well stirred and heating is continued for about 1 to 2 hours. After cooling the mixture with ice-water, it is made basic in order to facilitate isolation of the product.

Preferably the reaction is heated to about 50° and then the peroxydisulfate is added. The addition of the peroxydisulfate must be at a rate to control the exotherm of the reaction. Once the addition of peroxydisulfate is complete, the reaction is stirred or agitated for about 10 minutes to 1 hour at a temperature from 70°–80° C. In order to maximize the yield of product, the temperature of the reaction must be maintained below 80°. It is also important to keep the reaction mixture well agitated. Therefore, it is advisable to use an air-driven stirrer and Morton flask for the reaction.

The products of this process are most easily isolated by using a base, such as ammonium hydroxide, sodium hydroxide, sodium carbonate, potassium carbonate, and the like, which makes the reaction solution basic. The products are then extracted with an inert organic solvent, such as methylene chloride, and the like, and dried with magnesium sulfate, sodium sulfate, and the like. The concentrated solutions are then chromatographed, if necessary, over silica gel with eluting solvents composed of mixtures of alkanes and ethers, such as hexanes and ethyl ether.

Certain substituted pyridazines, such as 3-halo-6-alkylpyridazines, can be prepared by established routes starting with γ-ketoacids. The ketoacid is reacted with hydrazine by heating in a solvent. This reaction results in the cyclization and the formation of a substituted dihydropyridazinone. The dihydropyridazinone compound is then oxidized to form a pyridazinone, using a reagent, such as bromine, in a solvent, such as acetic acid. Halogenation of the pyridazinone, using for example, phosphorous oxychloride, forms the desired substituted pyridazine.

Alkoxy or aryloxy derivatives can be prepared from the reaction of the alkali metal salt of the corresponding alcohol or phenol with a pyridazine, such as 3,6-dichloropyridazine. This reaction is conducted in a solvent, such as the corresponding alcohol, DMF, DMSO, and the like. The salt used in the reaction can be preformed, for example, by the reaction of the alcohol and sodium hydride, or can be generated in situ. Typically, the temperature of the reaction is from room temperature to about the reflux temperature of the solvent.

The following examples are illustrative of this invention. However, these examples are not to be construed as limitations on the invention. The temperatures are reported in degrees Celsius.

EXAMPLE 1

N'-[6-(1,1-Dimethylethyl)-3-pyridazinyl]-N,N-dimethylurea

To 2.70 grams (g) (0.0331 mole) of dimethylamine hydrochloride in 50 milliliters (ml) of benzene was added 4.12 g (0.0331 mole) of DBN. After stirring the reaction mixture for about 10 minutes at room temperature, 3.0 g (0.011 mole) of phenyl N-[6-(1,1-dimethylethyl)-3-pyridazinyl]carbamate was added. The reaction was stirred at room temperature, filtered, and concentrated. Then the mixture was chromatographed on silica gel with ethyl acetate as the eluent, using chloroform to solubilize the mixture.

After concentrating the fraction, an offwhite crystalline material was obtained weighing 1.4 g (57%), which had a melting point (MP) of 143°–147°. The molecular weight (MW) of the product was 222.28 and nuclear magnetic resonance (NMR) and mass spectra were consistent with the structure of the desired product.

The following elemental analysis was obtained:

Calculated for $C_{11}H_{18}N_4O$: Theory: C, 59.44; H, 8.16; N, 25.20; O, 7.20. Found: C, 59.58; H, 8.22; N, 24.98; O, 7.43.

The following examples were prepared using the general procedure of Example 1.

EXAMPLE 2

N,N-Dimethyl-N'-[6-(trifluoromethyl)-3-pyridazinyl]urea

Yield=0.93 g (100%)

MP=153.5°–155°

NMR and mass spectra were consistent with the structure of the desired product.

MW=234.18
Calculated for C$_8$H$_9$F$_3$N$_4$O: Theory: C, 41.03; H, 3.87; N, 23.92. Found: C, 41.12; H, 3.75; N, 24.15.

EXAMPLE 3

N'-[6-(1-Ethyl-1-methylpropyl)-3-pyridazinyl]-N,N-dimethylurea

Yield=1.5 g (100%)
MP=125°–127.5°
NMR and mass spectra were consistent with the structure of the desired product.
MW=250.34
Calculated for C$_{13}$H$_{22}$N$_4$O: Theory: C, 62.37; H, 8.86; N, 22.38. Found: C, 62.61; H, 8.92; N, 22.53.

The following example was prepared using the general procedure of Example 1, except DBU was used instead of DBN.

EXAMPLE 4

N'-(6-Chloro-3-pyridazinyl)-N,N-dimethylurea

Yield=1.0 g (62%)
MP=166°–169°
NMR, infrared (IR), and mass spectra were consistent with the structure of the desired product.
MW=200.63
Calculated for C$_7$H$_9$ClN$_4$O: Theory: C, 41.91; H, 4.52; N, 27.93; Cl, 17.67. Found: C, 41.91; H, 4.25; N, 27.98; Cl, 17.63.

The following examples were prepared using the general procedure of Example 4, except chloroform was used as a solvent in addition to benzene.

EXAMPLE 5

N'-[6-Chloro-5-(1,1-dimethylethyl)-3-pyridazinyl]-N,N-dimethylurea

Yield=2.1 g (76%)
MP=118°–122°
NMR, IR, and mass spectra were consistent with the structure of the desired product.
MW=256.74
Calculated for C$_{11}$H$_{17}$ClN$_4$O: Theory: C, 51.46; H, 6.67; N, 21.82; O. 6.23; Cl, 13.81. Found: C, 51.23; H, 6.68; N, 21.56; O, 6.43; Cl, 14.00.

EXAMPLE 6

N-[6-Chloro-5-(1,1-dimethylethyl)-3-pyridazinyl]-N,N',N'-trimethylurea

Yield=0.3 g (18%)
MP=77°–80.5°
Mass spectrum was consistent with the structure of the desired product.
MW=270.76
Calculated for C$_{12}$H$_{19}$ClN$_4$O: Theory: C, 53.23; H, 7.07; N, 20.69. Found: C, 53.12; H, 6.83; N, 20.45.

The following example was prepared using the general procedure of Example 1, except triethylamine was used instead of DBN.

EXAMPLE 7

N'-[6-(1,1-Dimethylethyl)-3-pyridazinyl]-N-methoxy-N-methylurea

Yield=0.38 g (25%)
MP=79°–81°
NMR, IR, and mass spectra were consistent with the structure of the desired product.
MW=238.28
Calculated for C$_{11}$H$_{18}$N$_4$O$_2$: Theory: C, 55.45; H, 7.61; N, 23.51. Found: C, 55.72; H, 7.40; N, 23.27.

The following examples were prepared using the general procedure of Example 1, except toluene was used as the solvent and DBN was not used.

EXAMPLE 8

N'-[6-(1,1-Dimethylethyl)-3-pyridazinyl]-N-2,2-(dimethoxy)ethyl]-N-methylurea

Yield=3.4 g (82%)
MP=112°–114°
NMR, IR, and mass spectra were consistent with the structure of the desired product.
MW=296.36
Calculated for C$_{14}$H$_{24}$N$_4$O$_3$: Theory: C, 56.74; H, 8.16; N, 18.90; O, 16.20. Found: C, 56.99; H, 8.32; N, 10.16; O, 16.26.

EXAMPLE 9

N'-(6-Chloro-3-pyridazinyl)-N-[2,2-(dimethoxy)ethyl]-N-methylurea

Yield=1.22 g (92%)
MP=110°–111.5°
NMR, IR, and mass spectra were consistent with the structure of the desired product.
MW=274.71
Calculated for C$_{10}$H$_{15}$ClN$_4$O$_3$: Theory: C, 43.72; H, 5.50; N, 20.39; O, 17.47; Cl, 12.91. Found: C, 43.85; H, 5.24; N, 20.54; O, 17.53; Cl, 13.07.

EXAMPLE 10

N'-[6-Chloro-5-(1,1-dimethylethyl)-3-pyridazinyl]-N'-[2,2-(dimethoxy)ethyl-N-methylurea Yield=5.7 g (100%)
MP=75°–80°
NMR, IR, and mass spectra were consistent with the structure of the desired product.
MW=330.81
Calculated for C$_{14}$H$_{23}$ClN$_4$O$_3$: Theory: C, 50.83; H, 7.01; N, 16.94; O, 14.51; Cl, 10.72. Found: C, 50.55; H, 6.77; N, 16.67; O, 14.68; Cl, 10.45.

EXAMPLE 11

N'-[6-Chloro-5-(1,1-dimethylbutyl)-3-pyridazinyl]-N-[2,2-(dimethoxy)ethyl]-N-methylurea Yield=0.73 g (92%)
NMR spectrum was consistent with the structure of the desired product.
MW=358.87

EXAMPLE 12

N'-[6-Chloro-5-(1,1-dimethylethyl)-3-pyridazinyl]-N-methyl-N-(1-methyl-2-propenyl)urea Yield=0.65 g (83%)
MP=118°–120°
NMR and mass spectra were consistent with the structure of the desired product.
MW=296.80
Calculated for C$_{14}$H$_{21}$ClN$_4$O: Theory: C, 56.66; H, 7.13; N, 18.88. Found: C, 56.88; H, 6.94; N, 18.84.

EXAMPLE 13

N'-[6-Chloro-5-(1,1-dimethylethyl)-3-pyridazinyl]-N-methyl-N-(2-methyl-2-propenyl)urea Yield = 2.2 g (86%)
NMR and mass spectra were consistent with the structure of the desired product.
MW = 296.8
Calculated for $C_{14}H_{21}ClN_4O$: Theory: C, 56.66; H, 7.13; N, 18.88. Found: C, 56.93; H, 7.38; N, 18.97.

EXAMPLE 14

N-[6-Chloro-5-(1,1-dimethylethyl)-3-pyridazinyl]-N'-(2-hydroxyethyl)urea

Yield = 1.20 g (67%)
MP = 170°–172°
NMR, IR, and mass spectra were consistent with the structure of the desired product.
MW = 272.74
Calculated for $C_{11}H_{17}ClN_4O_2$: Theory: C, 48.44; H, 6.28; N, 20.54. Found: C, 48.50; H, 6.45; N, 20.50.

EXAMPLE 15

N'-[6-Chloro-5-(1,1-dimethylethyl)-3-pyridazinyl]-N-(2-hydroxyethyl)-N-methylurea Yield = 1.58 g (41%)
MP = 160°–160.5°
NMR, IR, and mass spectra were consistent with the structure of the desired product.
MW = 286.76
Calculated for $C_{12}H_{19}ClN_4O_2$: Theory: C, 50.26; H, 6.68; N, 19.54. Found: C, 50.54; H, 6.48; N, 19.71.

EXAMPLE 16

N'-[6-Chloro-5-(1,1-dimethylethyl)-3-pyridazinyl]-N-methoxy-N-2-propenylurea

Yield = 1.1 g (86%)
NMR and mass spectra were consistent with the structure of the desired product.
MW = 298.77
Calculated for $C_{13}H_{19}ClN_4O_2$: Theory: C, 52.26; H, 6.41; N, 18.75. Found: C, 52.70; H, 6.22; N, 18.13.

EXAMPLE 17

N'-[6-Chloro-5-(1,1-dimethylethyl)-3-pyridazinyl]-N-(2-propenyl)-N-phenylurea

Yield = 2.0 g (76%)
NMR and mass spectra were consistent with the structure of the desired product.
MW = 344.84
Calculated for $C_{18}H_{21}ClN_4O$: Theory: C, 62.69; H, 6.14; N, 16.25. Found: C, 62.44; H, 6.03; N, 16.11.

EXAMPLE 18

N'-[6-Chloro-5-(1,1-dimethylethyl)-3-pyridazinyl]-N-[(2,2-diethoxy)ethyl]-N-phenylmethylurea Yield = 1.83 g (73%)
NMR and mass spectra were consistent with the structure of the desired product.
MW = 434.96
Calculated for $C_{22}H_{31}ClN_4O_3$: Theory: C, 60.8; H. 7.2; N, 12.9. Found: C, 59.5; H, 7.4; N, 14.8.

EXAMPLE 19

N-[6-Chloro-5-(1,1-dimethylethyl)-3-pyridazinyl-N'-2-propenylurea

Yield = 0.61 g (63%)
MP = 172.5°–173.5°
NMR and mass spectra were consistent with the structure of the desired product.
MW = 268.75
Calculated for $C_{12}H_{17}ClN_4O$: Theory: C, 53.63; H, 6.38; N, 20.85. Found: C, 53.66; H, 6.55; N, 20.91.

EXAMPLE 20

[6-Chloro-5-(1,1-dimethylethyl)-3-pyridazinyl]urea

Yield = 1.32 g (88%)
MP = 241°–242°
NMR, IR, and mass spectra were consistent with the structure of the desired product.
MW = 228.68
Calculated for $C_9H_{13}ClN_4O$: Theory: C, 47.27; H, 5.73; N, 24.50. Found: C, 47.49; H, 5.70; N, 24.30.

EXAMPLE 21

N'-[6-(4-Chlorophenyl)-3-pyridazinyl]-N-methyl-N-2-propenylurea

Yield = 1.1 g (68%)
MP = 140°–150°
NMR and mass spectra were consistent with the structure of the desired product.
MW = 302.76
Calculated for $C_{15}H_{15}ClN_4O$: Theory: C, 59.51; H, 4.99; N, 18.50. Found: C, 63.43; H, 6.16; N, 14.20.

EXAMPLE 22

N-[6-Chloro-5-(1,1-dimethylethyl)-3-pyridazinyl]-1-piperidinecarboxamide

Yield = 1.63 g (84%)
MP = 176°–178°
NMR, IR, and mass spectra were consistent with the structure of the desired product.
MW = 296.80
Calculated for $C_{14}H_{21}ClN_4O$:
Theory: C, 56.66; H, 7.13; N, 18.88.
Found: C, 56.78; H, 7.25; N, 18.74.

EXAMPLE 23

N-[[[6-Chloro-5-(1,1-dimethylethyl)-3-pyridazinyl]-amino]carbonyl]-N-methylglycine One gram (0.00327 mole) of phenyl N-[6-chloro-5-(1,1-dimethylethyl)-3-pyridazinyl]carbamate and 0.505 g (0.00329 mole, 1.00 equivalent) of sarcosine ethyl ester hydrochloride in 150 ml of dry toluene were heated at reflux for about 2.5 hours. After cooling, the solution was diluted with 600 ml of ether and extracted with three 50-ml portions of 0.25N sodium hydroxide. Then it was washed with a 50-ml portion of saturated brine and dried with magnesium sulfate.

After acidification and extraction of the basic aqueous washes:
Yield = 0.54 g (55%)
MP = 169° (dec)
NMR, IR, and mass spectra were consistent with the structure of the desired product.
Calculated for $C_{12}H_{17}ClN_4O_3$: Theory: C, 47.93; H, 5.70; N, 18.63. Found: C, 48.08; H, 5.92; N, 18.45.

The following examples were prepared using the general procedure of Example 1, except toluene was used as the solvent and DBN was not used.

EXAMPLE 24

N'-[6-Chloro-5-(1,1-dimethylethyl)-3-pyridazinyl]-N-(1-methylethyl)-N-2-propenylurea Yield=5.88 g (65%)
MP=110°-112°
NMR, IR, and mass spectra were consistent with the structure of the desired product.
MW=310.5
Calculated for $C_{15}H_{23}ClN_4O$: Theory: C, 57.96; H, 7.46; N, 18.02. Found: C, 57.74; H, 7.34; N, 18.29.

EXAMPLE 25

N'-[6-Chloro-5-(1,1-dimethylethyl)-3-pyridazinyl]-N-ethyl-N-2-propenylurea

Yield=2.6 g (87%)
MP=75°-77°
NMR, IR, and mass spectra were consistent with the structure of the desired product.
MW=296.5
Calculated for $C_{14}H_{21}ClN_4O$: Theory: C, 56.66; H, 7.13; N, 18.88; Cl, 11.94. Found: C, 56.71; H, 6.95; N, 18.91; Cl, 11.67.

EXAMPLE 26

N-Methyl-N'-(6-phenoxy-3-pyridazinyl)-N-2-propenylurea

Yield=0.6 g (74%)
MP=88°-88.5°
NMR and mass spectra were consistent with the structure of the desired product.
MW=284.31
Calculated for $C_{15}H_{16}N_4O_2$: Theory: C, 63.37; H, 5.67; N, 19.71. Found: C, 63.17; H, 5.41; N, 19.51.

EXAMPLE 27

N'-[6-Chloro-4,5-dimethyl-3-pyridazinyl]-N-[2,2-(dimethoxy)ethyl]-N-methylurea

Yield=1.0 g (44%)
MP=128.5°-131°
NMR spectrum was consistent with the structure of the desired product.

The following example was prepared using the general procedures described above, except benzene was used as the solvent.

EXAMPLE 28

N'-[6-Chloro-4-(1,1-dimethylethyl)-3-pyridazinyl-N-[2,2-(dimethoxy)ethyl]-N-methylurea Yield=0.21 g (71%)
NMR, IR, and mass spectra were consistent with the structure of the desired product.
MW=434.92

EXAMPLE 29

N-[6-Chloro-5-(1,1-dimethylethyl)-3-pyridazinyl]-N'-methylurea

To a mixture of 1.3 g of (0.007 mole) of 3-amino-6-chloro-5-(1,1-dimethylethyl)pyridazine in 65 ml of methylene chloride was added one drop of triethylamine and 0.8 g (0.014 mole, 2.0 equivalents) of methyl isocyanate. The mixture was stirred at room temperature for about 18 hours. Additional methyl isocyanate (0.8 g, 0.140 mole, 2.0 equivalents) was added and about 3 hours later, the solution was diluted to 400 ml using methylene chloride. The solution was washed with four 40-ml portions of 1.0N hydrochloric acid and 50 ml of water, and was then dried with magnesium sulfate.

After concentration, 0.85 g (32%) of a white powder was collected, which had a melting point of 210°-211°. The molecular weight was 242.71 and NMR, IR, and mass spectra were consistent with the structure of the desired product.

The following elemental analysis was obtained:
Calculated for $C_{10}H_{15}ClN_4O$: Theory: C, 49.49; H, 6.23; N, 23.08. Found: C, 49.67; H, 6.26; N, 22.86.

The following example was prepared using the general procedure of Example 29.

EXAMPLE 30

N-[6-Chloro-5-(1,1-dimethylethyl)-3-pyridazinyl]-N,N'-dimethylurea

Yield=1.27 g (66%)
MP=150°-154.5°
NMR, IR, and mass spectra were the consistent with the structure of the desired product.
MW=256.74
Calculated for $C_{11}H_{17}ClN_4O$: Theory: C, 51.46; H, 6.67; N, 21.82; Cl, 13.81. Found: C, 51.63; H, 6.78; N, 22.09; Cl, 13.69.

EXAMPLE 31

N'-[6-Chloro-5-(1,1-dimethylethyl)-3-pyridazinyl]-N-methoxy-N-methylurea

A solution of 2.0 g (0.0108 mole) of 3-amino-6-chloro-5-(1,1-dimethylethyl)pyridazine in 40 ml of dry pyridine was kept between 0° and 3°. To this solution was added in a dropwise manner, 1.40 g (0.0113 mole, 1.05 equivalents) of N-methoxy-N-methylcarbamyl chloride. After allowing the solution to warm to room temperature for about 2 hours, it was concentrated in vacuo at 40°, resulting in a semisolid.

The semisolid was triturated in a 40/60 mixture of hexanes and ethyl acetate. The filtrate was washed with water, dried with magnesium sulfate, and was concentrated to an oil, which was chromatographed on silica gel using a 90/10 ration of methylene chloride and ethyl acetate as the eluent.

The resulting product weighed 1.45 g (49%) with a molecular weight of 272.74. NMR, IR, and mass spectra were consistent with the structure of the desired product.

The following elemental analysis was obtained:
Calculated for $C_{11}H_{17}ClN_4O_2$: Theory: C, 48.44; H, 6.28; N, 20.54; 0, 11.73; Cl, 13.00. Found: C, 48.15; H, 6.31; N, 20.34; 0, 11.95; Cl, 12.81.

EXAMPLE 32

N-[2-(Acetyloxy)ethyl]-N'-[6-chloro-5-(1,1-dimethylethyl)-3-pyridazinyl]-N-methylurea A solution of 1.0 g (0.00349 mole) of N'-[6-chloro-5-(1,1-dimethylethyl)-3-pyridazinyl]-N-hydroxyethyl-N-methylurea in 25 ml of methylene chloride, and 0.276 g (0.00349 mole) of dry pyridine was prepared. Keeping the temperature between 15° and 20°, 0.279 g (0.00349 mole) of 98% acetyl chloride was added. The contents were allowed to stir for about 16 hours at room temperature. The reaction mixture was concentrated to an oil, which was partitioned between ether and water. The layers were separated and the organic layer was washed with water and dried with magnesium sulfate.

After concentrating the solution to an oil, the oil was chromatographed on silica gel using a 75/25 ratio of methylene chloride and ethyl acetate as the eluent.

The product weighed 0.62 g (54%) and the molecular weight was 328.80. NMR, IR, and mass spectra were consistent with the structure of the desired product.

The following elemental analysis was obtained:
Calculated for $C_{14}H_{21}ClN_4O_3$: Theory: C, 51.14; H, 6.44; N, 17.04. Found: C, 50.97; H, 6.55; N, 17.16.

Also provided by this invention is a method of inhibiting the growth of unwanted vegetation which comprises contacting the vegetation or the soil in which the vegetation is growing with a herbicidally-effective amount of a compound of the formula (II). The pyridazinylureas provided by this invention exhibit terrestrial herbicidal activity and accordingly are useful in the control and elimination of unwanted vegetative growth.

The herbicides of the invention are effective terrestrially in both preemergent and postemergent control of a wide variety of grasses, broadleaf weeds, and sedges. Commonly encountered unwanted terrestrial vegetation, which is subject to control with the herbicidal compounds of this invention include:
Wild Oat (*Avena fatua*)
Catchweed Bedstraw (*Galium aparine*)
Scentless Mayweed (*Matricaria inodora*)
Ladysthumb (*Polygonum persicaria*)
Common Chickweed (*Stellaria media*)
Ivyleaf Speedwell (*Veronica hederaefolia*)
Blackgrass (*Alopecurus myosuroides*)
Chrysanthemum (Chrysanthemum spp.)
Common Purslane (*Portulaca oleracea*)
Sida (Sida spp.)
Bristly Starbur (*Acanthospermum hispidum*)
Goosegrass (*Eleusine indica*)
Smooth Pigweed (*Amaranthus hybridus*)
Alexandergrass (*Brachiaria plantaginea*)
Tall Morningglory (*Ipomoea purpurea*)
Common Lambsquarter (*Chenopodium album*)
Green Smartweed (*Polygonum acabrum*)
Green Foxtail (*Setaria viridis*)
Redroot Pigweed (*Amaranthus petroflexus*)
Wild Buckwheat (*Polygonum convolvulus*)
Brazil Calalilly (*Richardia brasiliensis*)
Natal Grass (*Rhynchelytrum roseum*)
Ryegrass (*Lolium rigidum*)
Kapeweed (*Cryptostemma calendula*)
Purple Loosestrife (*Lythrum salicaria*)
Wild Radish (*Raphanus raphanistrum*)
Wireweed (*Polygonum aviculare*)
Henbit (*Lamium amplexicaule*)
Wild Mustard (*Brassica kaber*)
Barnyard Grass (*Echinochloa crus-galli*)
Foxtail Millet (*Setaria italica*)
Velvetleaf (*Abutilon theophrasti*)
Indian Mustard (*Brassica juncea*)
Birdseye Speedwell (*Veronica persica*)
Canada Thistle (*Cirsium arvense*)
Wild Chamomile (*Matricaria chamomilla*)
Annual Bluegrass (*Poa annua*)
Buttercup (Ranunculus spp.)
Field Speedwell (*Veronica agrestis*)
Field Violet (*Viola arvensis*)
Field Pennycress (*Thlaspi arvense*)
Wild Violet (*Viola tricolor*)
Shirley Poppy (*Papaver rhoeas*)
Field Poppy (*Papaver dubium*)
Foolsparsley (*Aethusa cynapium*)
Field Chickweed (*Cerastium arvense*)
Southern Sandbur (*Cenchrus echinatus*)
Large Crabgrass (*Digitaria sanguinalis*)
Cheat (*Bromus secalinus*)
Morningglory (Ipomea spp.)
Common Ragweed (*Ambrosia artemisiifolia*)
Common Milkweed (*Asclepias syriaca*)
Giant Foxtail (*Setaria faberi*)
Common Cocklebur (*Xanthium pensylvanicum*)
Spurred Anoda (*Anoda cristata*)
Sicklepod (*Cassia obtusifolia*)
Yellow Nutsedge (*Cyperus esculentus*)
Jimsonweed (*Datura stramonium*)
Prickly Sida (*Sida spinosa*)
Corn Gromwell (*Lithospermum arvense*)
Yellow Foxtail (*Setaria glauca*)
Tansymustard (*Descurania pinnata*)
Pepperweed (Lepidium spp.)
Bromegrass (Bromus spp.)
Garden Spurge (*Euphorbia hirta*)
Crowfootgrass (*Dactyloctenium aegyptium*)
Florida Beggarweed (*Desmodium tortuosum*)
Spotted Spurge (*Euphorbia maculata*)
Smallflower Morningglory (*Jacquemontia tamnifolia*)
Browntop Millet (*Panicum ramosum*)
Coast Fiddleneck (*Amsinckia intermedia*)
Wild Turnip (*Brassica campestris*)
Black Mustard (*Brassica nigra*)
Shepherdspurse (*Capsella bursa-pastoris*)
Italian Ryegrass (*Lolium multiflorum*)
London Rocket (*Sisymbrium irio*)
Redmaids Rockpurslane (*Calandrinia caulescens*)
Common Groundsel (*Senecio vulgaris*)
Ivyleaf Morningglory (*Ipomoed hederacea*)
Fall Panicum (*Panicum dichotomiflorum*)
Powell Amaranth (*Amaranthus powellii*)
Texas Panicum (*Panicum texanum*)
Hemp Sesbania (*Sesbania exaltata*)
Annual Sowthistle (*Sonchus oleraceus*)
Field Bindweed (*Convolvulus arvensis*)
Erect Knotweed (*Polygonum erectum*)
Venice Mallow (*Hibiscus trionum*)
Zinnia (*Zinnia elegens*)
Nightshade (Solanum spp.)

The present compounds have also been found safe on a wide variety of desirable plant species, thereby exhibiting their unique selective capacity. Representative examples of relatively tolerant plant species, depending on the concentration of active ingredient employed and the means of application, include the following:
Corn (*Zea mays*)
Wheat (*Triticum aestivum*)
Soybean (*Glycine max*)
Rice (*Oryza sativa*)
Barley (*Hordeum vulgare*)
Cotton (*Gossypium hirsutum*)
Sorghum (*Sorghum vulgare v. saccharatum*)
Sugarcane (*Saccharum officinarum*)
Peanut (*Arachis hypogaea*)
Alfalfa (*Medicago sativa*)
Cucumber (*Cucumis sativus*)
Tomato (*Lycopersicon esculentum*)
Sugar Beet (*Beta vulgaris*)

A test used to evaluate herbicidal efficacy was conducted at a compound concentration of 15 pounds per acre (16.8 kilograms per hectare). In this test a standard sand/soil mixture (1:1) was sterilized and added to separate containers and tomato, large crabgrass, and pigweed seeds were planted by row.

The test compounds were formulated for application by dissolving the compound into a solvent, containing acetone, ethanol, and a blend of anionic and nonionic surfactants. The solvent/compound solution was diluted with deionized water and applied postemergence to some planted containers and preemergence to others. Postemergent treatment was made 11 to 13 days after planting, while preemergent treatment was made one day after planting.

Following treatment the containers were moved to the greenhouse and watered as necessary. Observations were made 10 to 13 days after treatment using untreated control plants as standards. The degree of herbicidal activity was determined by rating the treated plants on a scale of 1 to 5. On this scale "1" indicates no injury, "2" is slight injury, "3" is moderate injury, "4" is severe injury, and "5" indicates death to the plant or no seedling emergence.

Table I, which follows, presents the terrestrial herbicidal activity of the compound at 15 pounds per acre (lb/A).

TABLE I

| | Terrestrial Herbicidal Activity Plant Species | | | | | |
|---|---|---|---|---|---|---|
| | Preemergence | | | Postemergence | | |
| Compound of Ex. No. | Tomato | Large Crab-grass | Pig-weed | Tomato | Large Crab-grass | Pig-weed |
| 1 | 1 | 1 | 1 | 5 | 4 | 5 |
| 2 | 1 | 1 | 1 | 1 | 1 | 1 |
| 3 | 1 | 1 | 1 | 1 | 1 | 1 |
| 4 | 5 | 3 | 4 | 2 | 1 | 1 |
| 5 | 2 | 1 | 3 | 5 | 5 | 5 |
| 8 | 4 | 4 | 4 | 4 | 3 | 5 |
| 9 | 1 | 2 | 3 | 2 | 3 | 2 |
| 10 | 2 | 1 | 3 | 5 | 5 | 5 |
| 12 | 1 | 1 | 1 | 5 | 5 | 5 |
| 13 | 1 | 1 | 1 | 2 | 5 | 1 |
| 14 | 1 | 1 | 1 | 1 | 1 | 1 |
| 15 | 5 | 4 | 5 | 5 | 5 | 5 |
| 17 | 1 | 1 | 1 | 1 | 1 | 2 |
| 19 | 1 | 1 | 1 | 1 | 1 | 2 |
| 20 | 1 | 1 | 1 | 1 | 1 | 1 |
| 23 | 1 | 1 | 1 | 3 | 3 | 2 |
| 30 | 1 | 3 | 4 | 5 | 5 | 5 |
| 31 | 2 | 1 | 4 | 5 | 5 | 5 |

The herbicidal activity of some of the compounds of the present invention was further evaluated at various application rates in a multiple species greenhouse test. Several additional weed and crop species were utilized to determine the herbicidal activity and selectivity of the test compounds. Lower concentrations of the test compounds were obtained by serial dilution of the above-described formulation with a mixture of the surfactant and deionized water. The compounds were evaluated according to the general procedure outlined above. See Table II. The following code was used in Table II:

A=Corn
B=Cotton
C=Soybean
D=Wheat
E=Alfalfa
F=Sugar Beet
G=Rice
H=Cucumber
I=Tomato
J=Barnyard Grass
K=Lambsquarter
L=Large Crabgrass
M=Mustard
N=Pigweed
O=Foxtail
P=Wild Oat
Q=Velvetleaf
R=Jimsonweed
S=Morningglory
T=Zinnia
[Note:
8 lb/A=8.96 kilograms per hectare (kg/ha)
4 lb/A=4.48 kg/ha
2 lb/A=2.24 kg/ha
1 lb/A=1.12 kg/ha.]

TABLE II

| Compound of Example No. | Appln. Rate lbs/A | PLANT SPECIES Preemergence | | | | | | | | | | | | | | | | | | | |
|---|---|---|---|---|---|---|---|---|---|---|---|---|---|---|---|---|---|---|---|---|---|
| | | A | B | C | D | E | F | G | H | I | J | K | L | M | N | O | P | Q | R | S | T |
| 1 | 8 | | | | | | | | | | | | 4 | | 4 | 3 | — | 5 | — | 1 | 2 |
| | 4 | 1 | 1 | 2 | 1 | 5 | 2 | 2 | 2 | 2 | 1 | — | 4 | 3 | 2 | 2 | 1 | 2 | 1 | 1 | 1 |
| | 2 | 1 | 1 | 1 | 1 | 1 | 1 | 1 | 1 | 1 | 1 | — | 4 | 3 | — | 3 | 1 | 3 | 1 | 1 | 2 |
| | 1 | 1 | 1 | 1 | 1 | 1 | 1 | 1 | 1 | 1 | 1 | — | 4 | 1 | — | 1 | 3 | 1 | 1 | 1 | 1 |
| 2 | 8 | 1 | | | | | | | | | | | 3 | — | 3 | 2 | — | 3 | — | 2 | 2 |
| 3 | 8 | 1 | | | | | | | | | | | 1 | — | 1 | 1 | — | 1 | — | 1 | 1 |
| 4 | 8 | | | | | | | | 1 | 1 | — | 2 | 1 | 3 | 1 | 1 | 1 | — | 1 | 2 |
| 5 | 8 | | | | | | | | 4 | 3 | — | 4 | 4 | 5 | 5 | 5 | 5 | — | 5 | 4 |
| | 4 | 2 | 1 | 1 | 3 | 5 | 4 | 2 | 5 | 2 | 2 | 4 | 3 | 4 | 4 | 4 | 4 | 3 | 3 | 3 | 4 |
| | 2 | 1 | 1 | 2 | 2 | 4 | 4 | 2 | 4 | 3 | 2 | 4 | 3 | 3 | 4 | 4 | 4 | 5 | 3 | 3 | 4 |
| | 1 | 1 | 1 | 1 | 1 | 3 | 4 | 2 | 4 | 3 | 2 | 3 | 4 | 3 | 4 | 4 | 4 | 4 | 4 | 4 | 4 |
| | 1 | 1 | 1 | 2 | 2 | 2 | 4 | 2 | 4 | 2 | 2 | 3 | 2 | 3 | 3 | 3 | 4 | 4 | 2 | 3 |
| | 0.5 | 1 | 1 | 1 | 1 | 1 | 2 | 2 | 2 | 2 | 1 | 2 | 2 | 3 | 3 | 2 | 3 | 2 | 2 | 2 |
| | 0.25 | 1 | 1 | 1 | 1 | 1 | 2 | 2 | 2 | 3 | 1 | 1 | 1 | 2 | 2 | 1 | 2 | 2 | 1 | 2 |
| 6 | 8 | | | | | | | | 3 | 1 | — | 4 | 5 | 4 | 3 | 2 | 3 | — | 3 | 2 |
| | 2 | 1 | 1 | 1 | 1 | 2 | 2 | 2 | 1 | 2 | 1 | 3 | 2 | 3 | 1 | 2 | 1 | 1 | 1 | 3 | 1 |
| | 1 | 1 | 1 | 1 | 1 | 1 | 2 | 2 | 2 | 1 | 1 | 2 | 1 | 3 | 1 | 2 | 1 | 1 | 1 | 3 | 1 |
| | 0.5 | 1 | 1 | 1 | 1 | 1 | 2 | 1 | 2 | 1 | 1 | 1 | 1 | 1 | 1 | 1 | 1 | 1 | 1 | 1 | 1 |
| 7 | 8 | 1 | | | | | | | | | | | 2 | — | 3 | 2 | — | 2 | — | 2 | 2 |

TABLE II-continued

PLANT SPECIES

| | | | | | | | | | | | | | | | | | | | | | |
|---|---|---|---|---|---|---|---|---|---|---|---|---|---|---|---|---|---|---|---|---|---|
| 12 | 8 | | | | | | | | 5 | 4 | — | 5 | 4 | 4 | 5 | 4 | 4 | — | 4 | 4 |
| | 4 | 2 | 1 | 1 | 1 | 5 | 4 | 3 | 2 | 4 | 4 | 5 | 5 | 5 | 5 | 5 | 2 | 5 | 5 | 3 | 2 |
| | 2 | 1 | 1 | 1 | 1 | 5 | 4 | 2 | 1 | 2 | 3 | 5 | 5 | 4 | 2 | 2 | 1 | 2 | 1 | 1 | 1 |
| | 1 | 1 | 1 | 1 | 1 | 3 | 1 | 1 | 1 | 1 | 1 | 4 | 3 | 1 | 2 | 1 | 1 | 1 | 2 | 1 | 1 |
| 13 | 8 | | | | | | | | | 3 | 4 | — | 4 | 4 | 4 | 5 | 4 | 5 | — | 4 | 4 |
| | 4 | 1 | 1 | 1 | 1 | 3 | 3 | 1 | 2 | 1 | 2 | 5 | 4 | 4 | 2 | 3 | 1 | 5 | 2 | 2 | 2 |
| | 2 | 1 | 1 | 1 | 1 | 3 | 1 | 1 | 1 | 1 | 2 | 5 | 2 | 5 | 1 | 3 | 1 | 5 | 1 | 2 | 2 |
| | 1 | 1 | 1 | 1 | 1 | 1 | 1 | 1 | 1 | 1 | 1 | 2 | 1 | 1 | 1 | 1 | 1 | 2 | 1 | 1 | 1 |
| 14 | 8 | | | | | | | | | 1 | 2 | — | 3 | 3 | 1 | 2 | 3 | 1 | — | 3 | 1 |
| 15 | 8 | | | | | | | | | 5 | 4 | — | 5 | 5 | 5 | 4 | 5 | 5 | — | 5 | 5 |
| | 4 | 2 | 3 | 4 | 2 | 4 | 4 | 5 | 5 | 5 | 3 | 5 | 3 | 5 | 5 | 4 | 3 | 5 | 4 | 5 | 5 |
| | 2 | 1 | 2 | 1 | 1 | 1 | 3 | 4 | 4 | 5 | 4 | 4 | 1 | 4 | 4 | 5 | 2 | 4 | 3 | 4 | 5 |
| | 1 | 1 | 1 | 2 | 2 | 2 | 1 | 2 | 3 | 4 | 3 | 5 | 2 | 4 | 3 | 4 | 2 | 3 | 2 | 3 | 2 |
| | 1 | 1 | 2 | 2 | 1 | 1 | 3 | 3 | 5 | 5 | 4 | 4 | 3 | 4 | 5 | 5 | 2 | 2 | 2 | 3 | 3 |
| | 0.5 | 1 | 1 | 1 | 1 | 1 | 2 | 2 | 2 | 3 | 3 | 5 | 2 | 3 | 5 | 5 | 1 | 1 | — | 2 | 2 |
| | 0.25 | 1 | 1 | 1 | 1 | 1 | 2 | 2 | 2 | 1 | 3 | 4 | 3 | 2 | 5 | 4 | 2 | 1 | 3 | 1 | 1 |
| | 0.25 | 1 | 1 | 2 | 2 | 1 | 3 | 3 | 2 | 3 | 3 | 4 | 2 | 2 | 5 | 5 | 1 | 1 | 2 | 1 | 1 |
| | 0.125 | 1 | 1 | 1 | 1 | 2 | 1 | 1 | 1 | 1 | 1 | 1 | 1 | 2 | 2 | 3 | 1 | 2 | 1 | 1 | 1 |
| | 0.06 | 1 | 1 | 1 | 1 | 1 | 1 | 1 | 1 | 1 | 1 | 1 | 1 | 1 | 1 | 1 | 1 | 1 | 1 | 1 | 1 |
| 16 | 8 | | | | | | | | | 4 | 2 | — | 4 | 4 | 5 | 5 | 2 | 5 | — | 4 | 2 |
| | 4 | 1 | 2 | 1 | 1 | 2 | — | 2 | 2 | 3 | 1 | 4 | 3 | 4 | 4 | 4 | 1 | 2 | 3 | 2 | 2 |
| | 2 | 1 | 1 | 1 | 1 | 1 | 1 | 1 | 1 | 1 | 1 | 3 | 3 | 2 | 4 | 2 | 1 | 2 | 2 | 1 | 1 |
| | 1 | 1 | 1 | 1 | 1 | 1 | 1 | 1 | 1 | 1 | 1 | 4 | 2 | 3 | 3 | 2 | 1 | 1 | 2 | 1 | 1 |
| 19 | 8 | | | | | | | | | 1 | 1 | — | 2 | 3 | 2 | 1 | 1 | 1 | — | 1 | 1 |
| 20 | 8 | | | | | | | | | 1 | 1 | — | 1 | 1 | 1 | 1 | 1 | 1 | — | 1 | 1 |
| 21 | 8 | | | | | | | | | 1 | 1 | — | 1 | 1 | 2 | 1 | 1 | 1 | — | 1 | 1 |
| 22 | 8 | | | | | | | | | 2 | 1 | — | 2 | 4 | 1 | 1 | 1 | 1 | — | 1 | 1 |
| 23 | 8 | | | | | | | | | 2 | 2 | — | 4 | 3 | 2 | 2 | 2 | 2 | — | 4 | 5 |
| | 4 | 1 | 1 | 1 | 1 | 1 | 1 | 1 | 1 | 2 | 1 | 1 | 2 | 1 | 1 | 2 | 1 | 1 | 2 | 2 | 2 |
| | 2 | 1 | 1 | 1 | 1 | 1 | 1 | 1 | 1 | 2 | 2 | 1 | 2 | 1 | 1 | 1 | 1 | 1 | 1 | 1 | 2 |
| | 1 | 1 | 1 | 1 | 1 | 1 | 1 | 1 | 1 | 1 | 1 | 1 | 1 | 1 | 1 | 1 | 1 | 1 | 1 | 1 | 1 |
| 24 | 8 | | | | | | | | | 2 | 1 | — | 2 | 3 | 1 | 2 | 1 | 2 | — | 1 | 1 |
| 25 | 8 | | | | | | | | | 2 | 4 | — | 4 | 4 | 4 | 5 | 2 | 4 | — | 2 | 2 |
| | 4 | 1 | 1 | 1 | 1 | 1 | 3 | 1 | 1 | 1 | 1 | 3 | 4 | 2 | 2 | 2 | 1 | 1 | 1 | 1 | 1 |
| | 2 | 1 | 1 | 1 | 1 | 1 | 2 | 2 | 1 | 1 | 1 | 1 | 4 | 2 | 3 | 2 | 1 | 1 | 1 | 1 | 1 |
| | 1 | 1 | 1 | 1 | 1 | 1 | 1 | 1 | 1 | 1 | 1 | 1 | 1 | 1 | 1 | 1 | 1 | 1 | 1 | 1 | 1 |
| 26 | 8 | | | | | | | | | 1 | 1 | — | 1 | 1 | 3 | 1 | 1 | 1 | — | 1 | 1 |
| 29 | 8 | | | | | | | | | 3 | 2 | — | 4 | 5 | 4 | 5 | 3 | 4 | — | 4 | 5 |
| | 4 | 1 | 1 | 1 | 1 | 3 | 3 | 1 | 2 | 2 | 2 | 2 | 3 | 2 | 3 | 2 | 1 | 1 | 1 | 1 | 1 |
| | 2 | 1 | 1 | 1 | 1 | 2 | 3 | 1 | 1 | 1 | 1 | 2 | 2 | 2 | 1 | 1 | 1 | 2 | 1 | 1 | 2 |
| | 1 | 1 | 1 | 1 | 1 | 1 | 1 | 1 | 1 | 1 | 1 | 1 | 1 | 1 | 1 | 1 | 1 | 1 | 1 | 1 | 1 |
| 30 | 8 | | | | | | | | | 3 | 3 | — | 4 | 4 | 5 | 4 | 4 | 5 | — | 4 | 3 |
| | 4 | 1 | 1 | 1 | 1 | 4 | 4 | 2 | 3 | 2 | 2 | 4 | 2 | 4 | 2 | 4 | 3 | 4 | 3 | 2 | 4 |
| | 2 | 1 | 1 | 1 | 1 | 4 | 4 | 2 | 2 | 2 | 2 | 4 | 3 | 4 | 2 | 3 | 2 | 2 | 4 | 3 | 2 |
| | 1 | 1 | 1 | 1 | 1 | 2 | 2 | 1 | 2 | 1 | 1 | 2 | 2 | 4 | 2 | 3 | 2 | 2 | 1 | 2 | 2 |
| 31 | 8 | | | | | | | | | 5 | 3 | — | 4 | 5 | 4 | 5 | 3 | 5 | — | 5 | 5 |
| | 4 | 2 | 1 | 2 | 3 | 5 | 4 | 2 | 4 | 4 | 3 | 4 | 4 | 4 | 4 | 4 | 4 | 4 | 4 | 4 | 5 |
| | 2 | 2 | 1 | 1 | 2 | 4 | 4 | 2 | 3 | 3 | 1 | 3 | 4 | 4 | 3 | 4 | 3 | 5 | 5 | 4 | 3 |
| | 1 | 1 | 1 | 1 | 1 | 4 | 4 | 2 | 2 | 3 | 1 | 2 | 3 | 3 | 3 | 2 | 2 | 3 | 2 | 2 | 2 |
| | 1 | 1 | 1 | 1 | 1 | 1 | 3 | 2 | 2 | 4 | 2 | 4 | 4 | 4 | 4 | 3 | 4 | 2 | 2 | 2 | 2 |
| | 0.5 | 1 | 1 | 1 | 1 | 1 | 2 | 2 | 2 | 3 | 3 | 2 | 3 | 2 | 2 | 2 | 1 | 2 | 1 | 1 | 1 |
| | 0.25 | 1 | 1 | 1 | 1 | 2 | 3 | 1 | 1 | 2 | 2 | 1 | 3 | 2 | 3 | 2 | 1 | 3 | 2 | 1 | 1 |
| 32 | 8 | | | | | | | | | 5 | 4 | — | 5 | 4 | 5 | 5 | 5 | 5 | — | 5 | 5 |
| | 4 | 4 | 2 | 4 | 4 | 5 | 5 | 4 | 5 | 5 | 4 | 5 | 5 | 5 | 5 | 5 | 5 | 5 | 5 | 5 | 5 |
| | 2 | 2 | 1 | 3 | 2 | 3 | 4 | 4 | 4 | 4 | 4 | 5 | 4 | 5 | 5 | 5 | 4 | 5 | 5 | 5 | 4 |
| | 1 | 2 | 1 | 1 | 1 | 1 | 2 | 2 | 1 | 3 | 4 | 5 | 2 | 3 | 5 | 4 | 4 | 4 | 5 | 4 | 3 |

| Compound of Example No. | Appln. Rate lbs/A | Postemergence | | | | | | | | | |
|---|---|---|---|---|---|---|---|---|---|---|---|
| | | I | J | A | L | M | N | O | P | Q | S | T |
| 1 | 8 | | | 1 | 3 | — | 5 | 2 | — | 4 | 3 | 3 |
| | 4 | | | 1 | 2 | — | 3 | 2 | — | 3 | 3 | 3 |
| | 2 | | | 1 | 1 | — | 3 | 1 | — | 3 | 2 | 3 |
| | 1 | | | 1 | 2 | — | 3 | 1 | — | 2 | 2 | 2 |
| 2 | 8 | | | 1 | 1 | — | 3 | 2 | — | 3 | 2 | 3 |
| 3 | 8 | | | 1 | 1 | — | 2 | 2 | — | 2 | 3 | 3 |
| 4 | 8 | 1 | 1 | — | 1 | 1 | 2 | 1 | 1 | 1 | 1 | 1 |
| 5 | 8 | 4 | 3 | — | 4 | 3 | 5 | 4 | 2 | 4 | 4 | 4 |
| | 4 | 4 | 2 | — | 3 | 4 | 4 | 3 | 2 | 2 | 4 | 4 |
| | 2 | 4 | 1 | — | 3 | 4 | 4 | 3 | 2 | 2 | 3 | 3 |
| | 1 | 4 | 2 | — | 3 | 4 | 4 | 3 | 2 | 3 | 2 | 4 |
| | 1 | 4 | 1 | — | 2 | 4 | 5 | 2 | 2 | 2 | 3 | 2 |
| | 0.5 | 2 | 1 | — | 2 | 3 | 3 | 2 | 2 | 3 | 3 | 2 |
| | 0.25 | 2 | 1 | — | 2 | 2 | 2 | 2 | 2 | 2 | 2 | 2 |
| 6 | 8 | 4 | 1 | — | 2 | 4 | 4 | 2 | 2 | 3 | 3 | 4 |
| | 2 | 2 | 2 | — | 2 | 4 | 1 | 3 | 2 | 2 | 3 | 2 |
| | 1 | 2 | 1 | — | 2 | 3 | 1 | 1 | 2 | 2 | 2 | 2 |
| | 0.5 | 2 | 1 | — | 1 | 2 | 1 | 1 | 1 | 2 | 2 | 1 |
| 7 | 8 | | | 2 | 2 | — | 4 | 2 | — | 3 | 2 | 2 |
| 12 | 8 | 5 | 4 | — | 3 | 5 | 4 | 5 | 3 | 2 | 5 | 5 |
| | 4 | 4 | 3 | — | 3 | 3 | 2 | 5 | 3 | 2 | 5 | 5 |

TABLE II-continued

PLANT SPECIES

|    |       |     |   |   |   |   |   |   |   |   |   |   |
|----|-------|-----|---|---|---|---|---|---|---|---|---|---|
|    | 2     | 3   | 2 | — | 4 | 4 | 2 | 4 | 1 | 2 | 4 | 3 |
|    | 1     | 1   | 2 | — | 2 | 3 | 1 | 3 | 1 | 1 | 4 | 2 |
| 13 | 8     | 2   | 3 | — | 4 | 4 | 2 | 4 | 2 | 2 | 2 | 2 |
|    | 4     | 2   | 1 | — | 2 | 3 | 3 | 3 | 2 | 2 | 2 | 2 |
|    | 2     | 1   | 1 | — | 2 | 2 | 2 | 3 | 1 | 1 | 2 | 2 |
|    | 1     | 1   | 1 | — | 1 | 1 | 1 | 2 | 1 | 1 | 1 | 1 |
| 14 | 8     | 1   | 1 | — | 1 | 2 | — | 1 | 1 | 1 | 1 | 1 |
| 15 | 8     | 4   | 2 | — | 3 | 5 | 3 | 4 | 1 | 5 | 3 | 2 |
|    | 4     | 5   | 2 | — | 4 | 5 | 5 | 4 | 2 | 5 | 4 | 5 |
|    | 2     | 5   | 2 | — | 2 | 5 | 4 | 3 | 1 | 5 | 5 | 4 |
|    | 1     | 2   | 1 | — | 3 | 4 | 3 | 2 | 1 | 2 | 2 | 2 |
|    | 1     |     |   |   |   |   |   |   |   |   |   |   |
|    | 0.5   |     |   |   |   |   |   |   |   |   |   |   |
|    | 0.25  |     |   |   |   |   |   |   |   |   |   |   |
|    | 0.25  |     |   |   |   |   |   |   |   |   |   |   |
|    | 0.125 |     |   |   |   |   |   |   |   |   |   |   |
|    | 0.06  |     |   |   |   |   |   |   |   |   |   |   |
| 16 | 8     | 5   | 4 | — | 5 | 4 | 5 | 4 | 3 | 4 | 5 | 5 |
|    | 4     | 3   | 4 | — | 4 | 4 | — | 4 | 4 | 5 | 4 | 3 |
|    | 2     | 2   | 3 | — | 3 | 3 | 3 | 4 | 4 | 1 | 3 | 2 |
|    | 1     | 2   | 1 | — | 3 | 2 | 2 | 2 | 2 | 1 | 2 | 2 |
| 19 | 8     | 1   | 1 | — | 2 | 2 | 2 | 1 | 1 | 1 | 1 | 1 |
| 20 | 8     | 1   | 1 | — | 1 | 1 | 1 | 1 | 1 | 1 | 1 | 1 |
| 21 | 8     | 1   | 1 | — | 1 | 2 | 2 | 2 | 1 | 1 | 1 | 1 |
| 22 | 8     | 1   | 1 | — | 1 | 1 | 1 | 1 | 1 | 1 | 1 | 1 |
| 23 | 8     |     |   |   |   |   |   |   |   |   |   |   |
|    | 4     |     |   |   |   |   |   |   |   |   |   |   |
|    | 2     |     |   |   |   |   |   |   |   |   |   |   |
|    | 1     |     |   |   |   |   |   |   |   |   |   |   |
| 24 | 8     | 1   | 1 | — | 1 | 1 | 1 | 1 | 1 | 1 | 1 | 1 |
| 25 | 8     | 4   | 2 | — | 3 | 5 | 3 | 3 | 2 | 1 | 4 | 4 |
|    | 4     | 3   | 1 | — | 2 | 4 | 3 | 3 | 1 | 1 | 3 | 3 |
|    | 2     | 2   | 1 | — | 1 | 3 | 1 | 3 | 2 | 1 | 2 | 2 |
|    | 1     | 2   | 1 | — | 1 | 2 | 1 | 2 | 2 | 1 | 2 | 2 |
| 26 | 8     | 2   | 1 | — | 1 | 2 | 2 | 1 | 1 | 2 | 2 | 2 |
| 29 | 8     | 2   | 1 | — | 2 | 3 | 1 | 2 | 1 | 2 | 2 | 2 |
|    | 4     |     |   |   |   |   |   |   |   |   |   |   |
|    | 2     |     |   |   |   |   |   |   |   |   |   |   |
|    | 1     |     |   |   |   |   |   |   |   |   |   |   |
| 30 | 8     | 4   | 2 | — | 2 | 4 | 4 | 2 | 2 | 2 | 2 | 3 |
|    | 4     | 4   | 1 | — | 3 | 5 | — | 3 | 2 | 3 | 4 | 5 |
|    | 2     | 4   | 1 | — | 3 | 4 | 2 | 2 | 2 | 2 | 3 | 3 |
|    | 1     | 3   | 1 | — | 2 | 4 | 2 | 2 | 2 | 2 | 2 | 2 |
| 31 | 8     | 5   | 4 | — | 5 | 5 | 5 | 4 | 4 | 5 | 5 | 5 |
|    | 4     | 5   | 4 | — | 4 | 5 | 5 | 4 | 5 | 4 | 4 | 5 |
|    | 2     | 4   | 3 | — | 4 | 4 | 5 | 4 | 4 | 4 | 3 | 4 |
|    | 1     | 4   | 1 | — | 3 | 4 | 5 | 3 | 3 | 3 | 3 | 3 |
|    | 1     | 4   | 3 | — | 4 | 4 | 4 | 4 | 3 | 4 | 2 | 4 |
|    | 0.5   | 3   | 1 | — | 2 | 3 | 2 | 2 | 2 | 2 | 2 | 2 |
|    | 0.25  | 2   | 1 | — | 2 | 2 | 2 | 2 | 2 | 1 | 2 | 2 |
| 32 | 8     | 2   | 1 | — | 4 | 5 | 4 | 2 | 1 | 2 | 5 | 3 |
|    | 4     | 2   | 1 | — | 2 | 4 | 4 | 3 | — | 1 | 4 | 3 |
|    | 2     | 1   | 1 | — | 1 | 4 | 4 | 3 | 1 | 1 | 3 | 3 |
|    | 1     | 1   | 1 | — | 1 | 3 | 3 | 1 | 1 | 1 | 4 | 2 |

Some of the compounds of this invention were further tested as described above. In addition to some of the species listed above, the compounds were evaluated against additional species.

The following code was used for the additional species in Tables III and IV:
U=Sorghum
V=Foxtail Millet
W=Nightshade
X=Sicklepod
Y=Wild Buckwheat However, plant injury ratings were made visually on a scale of 0–10 with 0 being no injury and 10 being plant death. The injury rating was multiplied by 10 to obtain a percent inhibition.

The results are recorded in Tables III and IV. (The compounds were pre-plant incorporated (PPI), or surface applied (SA) in the preemergent tests.)

TABLE III

PREEMERGENCE HERBICIDE TESTING
PERCENT CROP INJURY OR WEED CONTROL

| Compound of Example No. | Application Rate lbs/A | App. | A | B | D | G | V | J | P | C | B | N | S | Q | R | W |
|---|---|---|---|---|---|---|---|---|---|---|---|---|---|---|---|---|
| 5 | .50 | PPI | 0 | 0 | 80 | 40 | 70 | 40 | 80 | 0 | 0 | 90 | 80 | 90 | 100 | — |
|   | 1.00 | PPI | 20 | 40 | 90 | 50 | 98 | 80 | 95 | 30 | 0 | 100 | 95 | 100 | 100 | — |
|   | 2.00 | PPI | 50 | 70 | 100 | 100 | 100 | 90 | 100 | 70 | 20 | 100 | 100 | 100 | 100 | — |
| 5 | .50 | SA | 0 | 0 | 10 | 0 | 50 | 0 | 10 | 0 | 0 | 90 | 0 | 90 | 100 | 80 |
|   | 1.00 | SA | 10 | 0 | 20 | 20 | 80 | 60 | 30 | 20 | 0 | 98 | 40 | 98 | 100 | 98 |

TABLE III-continued

PREEMERGENCE HERBICIDE TESTING
PERCENT CROP INJURY OR WEED CONTROL

| Compound of Example No. | Application Rate lbs/A | App. | A | B | D | G | V | J | P | C | B | N | S | Q | R | W |
|---|---|---|---|---|---|---|---|---|---|---|---|---|---|---|---|---|
|  | 2.00 | SA | 40 | 0 | 50 | 60 | 90 | 95 | 60 | 50 | 0 | 100 | 80 | 100 | 100 | 98 |
| 15 | .06 | PPI | 0 | 0 | 0 | 0 | 0 | 0 | 0 | 0 | 0 | 0 | 0 | 0 | 0 | 50 |
|  | .12 | PPI | 10 | 0 | 0 | 0 | 0 | 0 | 0 | 0 | 0 | 0 | 40 | 0 | 0 | 60 |
|  | .25 | PPI | 0 | 0 | 50 | 0 | 60 | 30 | 80 | 70 | 0 | 100 | 95 | 30 | 100 | 100 |
|  | .25 | PPI | 20 | 0 | 40 | 20 | 50 | 30 | 40 | 20 | 10 | 90 | 90 | 40 | 95 | 95 |
|  | .50 | PPI | 40 | 50 | 90 | 98 | 100 | 98 | 100 | 98 | 95 | 100 | 100 | 100 | 100 | 100 |
|  | 1.00 | PPI | 80 | 100 | 100 | 98 | 100 | 100 | 100 | 98 | 98 | 100 | 100 | 100 | 100 | 100 |
| 15 | .12 | SA | 0 | 0 | 0 | 0 | 0 | 0 | 0 | 0 | 0 | 20 | 0 | 0 | 0 | 0 |
|  | .25 | SA | 0 | 0 | 0 | 0 | 50 | 10 | 0 | 0 | 0 | 70 | 0 | 0 | 20 | 98 |
|  | .50 | SA | 40 | 10 | 10 | 30 | 100 | 100 | 30 | 50 | 0 | 100 | 70 | 98 | 100 | 100 |
|  | .50 | SA | 0 | 0 | 0 | 0 | 98 | 40 | 0 | 20 | 0 | 80 | 50 | 0 | 98 | 98 |
|  | 1.00 | SA | 70 | 80 | 40 | 70 | 100 | 100 | 98 | 70 | 40 | 100 | 80 | 100 | 100 | 100 |
|  | 2.00 | SA | 80 | 100 | 70 | 90 | 100 | 100 | 95 | 95 | 70 | 100 | 100 | 100 | 100 | 100 |
| 30 | .50 | PPI | 0 | 0 | 20 | 20 | 0 | 0 | 60 | 30 | 0 | 0 | 50 | 90 | 60 | — |
|  | 1.00 | PPI | 0 | 0 | 80 | 60 | 60 | 40 | 70 | 50 | 10 | 40 | 80 | 100 | 100 | — |
|  | 2.00 | PPI | 0 | 20 | 95 | 70 | 80 | 80 | 98 | 90 | 60 | 90 | 98 | 100 | 100 | — |
| 30 | 1.00 | SA | 0 | 0 | 0 | 0 | 0 | 0 | 0 | 20 | 0 | 0 | 0 | 70 | 80 | 30 |
|  | 2.00 | SA | 0 | 0 | 0 | 50 | 30 | 0 | 40 | 30 | 0 | 50 | 0 | 80 | 80 | 80 |
|  | 4.00 | SA | 0 | 0 | 30 | 30 | 60 | 60 | 90 | 70 | 10 | 70 | 80 | 95 | 100 | 98 |
| 31 | .50 | PPI | 0 | 0 | 60 | 10 | 20 | 0 | 70 | 10 | 0 | 60 | 40 | 90 | 100 | — |
|  | 1.00 | PPI | 20 | 50 | 98 | 70 | 95 | 60 | 98 | 40 | 10 | 90 | 98 | 100 | 100 | — |
|  | 2.00 | PPI | 60 | 80 | 98 | 60 | 100 | 70 | 98 | 70 | 30 | 95 | 100 | 100 | 100 | — |
| 31 | .50 | SA | 0 | 0 | 0 | 0 | 40 | 0 | 10 | 0 | 0 | 80 | 0 | 40 | 90 | 98 |
|  | 1.00 | SA | 30 | 20 | 20 | 0 | 80 | 50 | 40 | 50 | 0 | 90 | 40 | 80 | 100 | 98 |
|  | 2.00 | SA | 40 | 20 | 30 | 30 | 98 | 60 | 50 | 80 | 20 | 90 | 30 | 100 | 100 | 100 |

TABLE IV

POSTEMERGENCE CROP TESTING
PERCENT CROP INJURY OR WEED CONTROL

| Compound of Example No. | Application Rate lbs/A | A | U | G | J | D | P | V | L | B | C | F | Y | R | S | M | W | N | X | Q | T |
|---|---|---|---|---|---|---|---|---|---|---|---|---|---|---|---|---|---|---|---|---|---|
| 5 | .50 | 0 | 0 | 10 | 15 | 10 | 0 | 15 | 30 | 15 | 30 | 90 | 90 | 60 | 50 | 50 | 20 | 40 | 30 | 60 | 30 |
|  | 1.00 | 0 | 0 | 25 | 10 | 15 | 10 | 40 | 50 | 30 | 30 | 70 | 0 | 95 | 70 | 80 | 0 | 60 | 50 | 70 | 50 |
|  | 2.00 | 15 | 10 | 15 | 10 | 15 | 20 | 50 | 50 | 30 | 50 | 70 | 0 | 95 | 80 | 90 | 20 | 30 | 60 | 80 | 80 |
| 12 | .50 | 0 | 10 | 15 | 0 | 0 | 0 | 10 | 10 | 30 | 60 | 50 | 30 | 80 | 20 | 30 | — | 0 | 30 | 0 | 20 |
|  | 1.00 | 15 | 30 | 15 | 25 | 10 | 20 | 30 | 20 | 100 | 60 | 60 | 90 | 40 | 20 | 30 | 0 | 0 | 30 | 30 | 50 |
|  | 2.00 | 15 | 20 | 15 | 25 | 20 | 0 | 80 | 40 | 100 | 100 | 40 | 60 | 80 | 60 | 50 | 0 | 30 | 100 | 0 | 30 |
| 15 | .50 | 0 | 10 | 10 | 0 | 0 | 0 | 10 | 15 | 70 | 100 | 100 | 20 | 60 | 50 | 60 | 30 | 50 | 15 | 40 | 0 |
|  | 1.00 | 0 | 0 | 10 | 0 | 0 | 0 | 30 | 0 | 100 | 100 | 100 | 20 | 100 | 50 | 100 | 40 | 50 | 30 | 40 | 0 |
|  | 2.00 | 0 | 0 | 40 | 0 | 0 | 0 | 80 | 20 | 100 | 100 | 100 | 30 | 100 | 100 | 85 | 40 | 60 | 15 | 40 | 40 |
| 30 | 1.00 | 20 | 40 | 20 | 0 | 10 | 0 | 0 | 0 | 30 | 30 | 90 | 0 | 60 | 30 | 80 | 60 | 50 | 40 | 40 | 20 |
|  | 2.00 | 30 | 20 | 20 | 15 | 40 | 20 | 20 | 20 | 40 | 50 | 100 | 20 | 100 | 40 | 100 | — | 95 | 70 | 60 | 60 |
|  | 4.00 | 60 | 30 | 20 | 20 | 40 | 20 | 20 | 60 | 40 | 50 | 90 | 20 | 100 | 60 | 100 | 60 | 95 | 70 | 50 | 50 |
| 31 | .50 | 15 | 30 | 10 | 0 | 10 | 40 | 40 | 60 | 15 | 40 | 95 | 90 | 70 | 50 | 50 | 70 | 15 | 60 | 60 | 50 |
|  | 1.00 | 40 | 60 | 20 | 30 | 20 | 50 | 75 | 80 | 30 | 50 | 95 | 60 | 95 | 80 | 99 | 70 | 80 | 50 | 100 | 100 |
|  | 2.00 | 80 | 80 | 50 | 60 | 40 | 60 | 100 | 95 | 60 | 90 | 95 | 90 | 100 | 85 | 99 | 60 | 100 | 100 | 100 | 100 |
| 32 | 1.00 | 0 | 0 | 0 | 0 | 0 | 0 | 0 | 0 | 20 | 10 | 90 | 50 | 30 | — | 60 | 50 | 60 | 10 | 0 | 0 |
|  | 2.00 | 0 | 0 | 0 | 0 | 0 | 0 | 0 | 0 | 90 | 30 | 90 | 60 | 40 | 30 | 80 | 50 | 80 | 50 | 20 | 30 |
|  | 4.00 | 0 | 0 | 30 | 0 | 0 | 20 | 40 | 70 | 100 | 70 | 100 | 80 | 90 | 100 | 95 | 40 | 90 | 50 | 70 | 50 |

The amount of herbicidal pyridazinylureas of the formula (II) to be employed in the method of this invention is an amount which is effective in controlling or inhibiting the growth of unwanted vegetation. Such herbicidal amount will depend upon a number of factors, including the method of application, formulation, soil texture, soil moisture content, the expected population of unwanted vegetation, degree of incorporation, the extent of growth control desired, and related factors. The rate of application normally will be from about 0.01 to about 10.0 pounds per acre, and preferably from about 0.25 to about 5.0 pounds per acre. These ranges are equivalent, respectively, to from about 0.011 to about 11.2 kilograms per hectare, and from about 0.28 to about 5.6 kilograms per hectare.

Terrestrial Herbicidal Formulations

The compounds of the present invention may also be formulated with a suitable agriculturally-acceptable carrier. Such compositions will contain from about 12 to about 95.0 percent by weight of the active ingredient, depending on the composition desired. Sprayable formulations are preferred, because of the rapidity and economy of application, and because the sprayed applications do not drift to untreated areas as would a dust, for example.

The most convenient formulations are in the form of concentrated compositions to be applied by spraying as water dispersions or emulsions containing in the range from about 0.1 percent to about 10 percent of the compounds. Water-dispersible or emulsifiable compositions may be either solids usually known as wettable powders, or liquids usually known as emulsifiable concentrates.

A typical wettable powder comprises an intimate mixture of a compound of the invention, an inert carrier, and surfactants. The concentration of the active compound is usually from about 25 percent to about 90 percent by weight. The inert carrier is usually chosen from among the attapulgite clays, the montmorillonite clays, the diatomaceous earths, or the purified silicates. Effective surfactants, comprising from about 0.5 percent to about 10 percent by weight of the wettable powder, are chosen from among the sulfonated lignins, the condensed napthalenesulfonates, and the alkyl sulfates.

A typical emulsifiable concentrate comprises from about 1 to about 6 pounds of a compound of the invention per gallon of liquid, dissolved in a mixture of organic solvents and emulsifiers. The organic solvent is chosen with regard to its solvency and its cost. Useful solvents include the aromatics, especially the xylenes and the heavy aromatic naphthas. Hydrophilic cosolvents such as cyclohexanone and isophorone may be included. Other organic solvents may also be used, including the terpenic solvents and kerosene. Suitable emulsifiers for emulsifiable concentrates are chosen from the alkylbenzenesulfonates, napthalenesulfonates, and nonionic surfactants such as alkylphenol adducts of polyoxyethylene, and are used at similar percentages as for wettable powders.

The compounds of this invention may be formulated as flowables or aqueous suspensions. A typical flowable formulation contains from about 12 to 75% by weight of the active ingredient, surfactants which are wetting and dispersing agents of the types used in wettable powder formulations and used at from 1 to 10 percent, about 5 to 10% of an antifreeze solution such as ethylene or propylene glycol, and a bulking or thickening agent. These thickeners may be natural water soluble gums, clays with gelling properties, cellulose derivatives and the like, and are used from about 0.5% to 5% of the product. The remainder of the formula is water. The product is prepared by grinding the slurry in a ball mill or sand mill to the desired particle size. Antifoam compounds, usually of the silicone type, may be added at 0.05% to 1% to control product foaming.

Solid, granular compositions are convenient for the application of compounds of this invention to the soil and will contain the active agent in an amount from about 0.1 to about 20% by weight. Granules comprise a compound of the invention dispersed on a granular inert carrier, such as coarsely ground clay of from about 0.1 to about 3 mm particle size. The compound is most conveniently applied to the clay by dissolving it in an inexpensive solvent and applying the solution to the sized clay in an appropriate solids mixer.

The formulated compounds are applied to plants in the manners conventional in agricultural chemistry. Sprayable compositions are easily applied by any of many types of sprayers available to the art. Self-propelled, tractor-mounted, and towed spray devices which apply the water-dispersed formulations through calibrated atomizing nozzles are available and effective. Metering appli-ators are also available which can apply accurately measured quantities of granular compositions ot the soil. The operator of the application equipment need only take care to adjust the equipment to apply an amount of the water-dispersed or granular formulation per acre which supplies the desired application rate of the compound, and to apply the amount uniformly to the plants to be treated.

The following detailed examples of formulations illustrate preferred aspects of the invention.

| Granule | |
|---|---|
| Ingredient | Percent by weight |
| Compound of Example 15 | 5.0 |
| Clay granule | 95.0 |

The compound is substantially dissolved in acetone or similar solvent, and the organic solution is sprayed onto the clay, which is in the form of chips. The mixture is then thoroughly blended and dried.

| Wettable Powder | |
|---|---|
| Ingredient | Percent by weight |
| Compound of Example 15 | 75.0 |
| Fuller's earth | 19.0 |
| Sulfonated lignin | 3.5 |
| Sodium lauryl sulfate | 2.5 |

The above ingredients are blended to uniformity and are ground in a hammer mill or air mill. The product is then reblended to a homogeneous free-flowing powder. The powder is dispersed in water and sprayed onto the weed-infested area.

| Emulsifiable Concentrate (1EC) | |
|---|---|
| Ingredient | Percent by weight |
| Compound of Example 15 | 13.0 |
| Sponto N500B, an emulsifier, from Witco Chemical Corp. | 12.0 |
| Dowanol PM, propylene glycol monomethyl ether, from Dow Chemical Co. | 25.0 |
| Xylene | 50.0 |
| | 100.0 |

The above ingredients are blended together to form the concentrate. The concentrate is then diluted and sprayed on the locus where control is desired.

| Wettable Powder (50 W) | |
|---|---|
| Ingredient | Percent by weight |
| Compound of Example 31 | 51.5 |
| Sellogen HR, an alkylnaphthalene sulfonate wetting agent, from Diamond Shamrock Chemical Co. | 5.0 |
| Polyfon O, a dispersant, from Westvaco Corp. | 5.0 |
| Zeolex F, a hydrated silicate, from J. M. Huber Corp. | 5.0 |
| Barden clay, clay from J. M. Huber Corp. | 33.5 |
| | 100.0 |

The above ingredients are blended to uniformity and are ground. The product is then reblended to a homogeneous free-flowing powder and dispersed in water.

We claim:

1. A compound of the formula

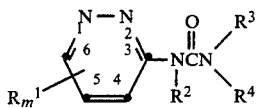

wherein
R$_2$ is hydrogen;
R$_3$ and R$_4$ are independently C$_1$–C$_3$ alkyl, C$_1$–C$_3$ alkoxy, C$_2$–C$_4$ alkenyl, hydroxy(C$_1$–C$_4$ alkyl) or (C$_1$–C$_6$ acyloxy)C$_1$–C$_6$ alkyl;
m is 1 or 2; and
when m is 1, R$^1$ represents 1,1dimethylethyl, and when m is 2, one R$^1$ represents 1,1-dimethylethyl and the other R$^1$ represents chloro.

2. A compound of claim 1 wherein R$_m^1$ is 6-chloro-5-(1,1-dimethylethyl).

3. The compound of claim 2 which is N'-[6-chloro-5-(1,1-dimethylethyl)-3-pyridazinyl]-N-methoxy-N-methylurea.

4. The compound of claim 2 which is N-[2-(acetyloxy)ethyl]-N'-[6-chloro-5-(1,1-dimethylethyl)-3-pyridazinyl]-N-methylurea.

5. The compound of claim 2 which is N'-[6-chloro-5-(1,1-dimethylethyl)-3-pyridazinyl]-N-(2-hydroxyethyl)-N-methylurea.

6. A method of inhibiting the growth of unwanted vegetation which comprises contacting the vegetation or the soil in which the vegetation is growing with an effective amount of a compound of the formula

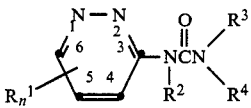

wherein
R$_2$ is hydrogen;
R$_5$ and R$_6$ are independpently hydrogen, C$_1$–C$_3$ alkyl, C$_1$–C$_3$ alkoxy, C$_2$–C$_4$ alkenyl, hydroxy (C$_1$–C$_4$ alkyl) or (C$_1$–C$_6$ acyloxy)C$_1$–C$_6$ alkyl;
n is 1 or 2; and
when n is 1, R$^1$ represents 1,1-dimethylethyl, and when n is 2, one R$^1$ represents 1,1-dimethylethyl and the other R$^1$ represents chloro.

7. The method of claim 6 employing a compound wherein R$_m^1$ is 6-chloro-5-(1,1-dimethylethyl).

8. The method of claim 7 wherein the compound is N'-[6-chloro-5-(1,1-dimethylethyl)-3-pyridazinyl]-N,N-dimethylurea.

9. The method of claim 7 wherein the compound is N'-[6-chloro-5-(1,1-dimethylethyl)-3-pyridazinyl]-N-methoxy-N-methylurea.

10. The method of claim 7 wherein the compound is N-[2-(acetyloxy)ethyl]-N'-[6-chloro-5-(1,1-dimethylethyl)-3-pyridazinyl]-N-methylurea.

11. The method of claim 7 wherein the compound is N'-6-chloro-5-(1,1-dimethylethyl)-3-pyridazinyl]-N-(2-hydroxyethyl)-N-methylurea.

12. A formulation which comprises a compound of claim 1 and an agriculturally-acceptable carrier therefor.

13. The formulation of claim 12 comprising a compound wherein R$_m^1$ is 6-chloro-5-(1,1-dimethylethyl).

14. The formulation of claim 13 wherein the compound is N'-[6-chloro-5-(1,1-dimethylethyl)-3-pyridazinyl]-N-methoxy-N-methylurea.

15. The formulation of claim 13 wherein the compound is N-[2-(acetyloxy)ethyl]-N'-[6-chloro-5-(1,1-dimethylethyl)-3-pyridazinyl]-N-methylurea.

16. The formulation of claim 13 wherein the compound is N'-[6-chloro-5-(1,1-dimethylethyl)-3-pyridazinyl]-N-(2-hydroxyethyl)-N-methylurea.

* * * * *

UNITED STATES PATENT AND TRADEMARK OFFICE
CERTIFICATE OF CORRECTION

PATENT NO. : 4,619,686
DATED : October 28, 1986
INVENTOR(S) : Riaz F. Abdulla et al.

It is certified that error appears in the above—identified patent and that said Letters Patent is hereby corrected as shown below:

On the first page, under OTHER PUBLICATIONS, the word "pyrdiazine" should be replaced with --pyridazine--.

In the Abstract, "noval" should be replaced with --novel--.

In Claim 1, the phrase "$R_2$ is hydrogen;" should be replaced with --$R^2$ is hydrogen;--.

In Claim 1, the phrase "$R_3$ and $R_4$ are independently" should be replaced with --$R^3$ and $R^4$ are independently--.

In Claim 1, the phrase "$R^1$ represents 1,1dimethylethyl " should be replaced with --$R^1$ represents 1,1-dimethylethyl--.

In Claim 6, within the structure, "$R^3$" should be replaced with --$R^5$--.

In Claim 6, within the structure, "$R^4$" should be replaced with --$R^6$--.

In Claim 6, the phrase, "$R_2$ is hydrogen;" should be replaced with --$R^2$ is hydrogen;--.

In Claim 6, the phrase, "$R_5$ and $R_6$ are independpently hydrogen," should be replaced with --$R^5$ and $R^6$ are independently hydrogen,--.

UNITED STATES PATENT AND TRADEMARK OFFICE
CERTIFICATE OF CORRECTION

PATENT NO. : 4,619,686

DATED : October 28, 1986

INVENTOR(S) : Riaz F. Abdulla et al.

It is certified that error appears in the above-identified patent and that said Letters Patent is hereby corrected as shown below:

In Claim 11, the phrase, "N'-6-chloro" should be replaced with --N'-[6-chloro--.

Signed and Sealed this

Twenty-third Day of August, 1988

Attest:

DONALD J. QUIGG

Attesting Officer

Commissioner of Patents and Trademarks